(12) United States Patent
Nau

(10) Patent No.: US 6,184,401 B1
(45) Date of Patent: Feb. 6, 2001

(54) ALPHA-FLUORO ALKYNOIC ACIDS WITH ANTICONVULSANT ACTIVITY

(76) Inventor: Heinz Nau, Lange-Hop-Strasse 45E, D-30559, Hannover (DE)

( * ) Notice: Under 35 U.S.C. 154(b), the term of this patent shall be extended for 0 days.

(21) Appl. No.: 09/337,912

(22) Filed: Jun. 22, 1999

Related U.S. Application Data

(60) Provisional application No. 60/090,270, filed on Jun. 22, 1998.

(51) Int. Cl.$^7$ ................................................ C07C 53/00
(52) U.S. Cl. ............................ 554/227; 554/150; 514/557
(58) Field of Search ................... 554/231, 150; 514/554

(56) References Cited

PUBLICATIONS

Tang, et al., 1997, "Time Course of α–Fluorinated Valproic Acid in Mouse Brain and Serum and its Effect on Synaptosomal γ–Aminobutyric Acid Levels in Comparison to Valproic Acid ", *Journal of Pharmacology and Experimental Therapeutics,* 282: 1163–1172.

Michel, et al., 1997, "No Evidence For Intramolecular Hydrogen Bonds in α–Fluorocarboxamides," *Liebigs Ann./Recueil,* 517–519.

Marie–Gabrielle Le Pironee, et al., 1997, "General and Simple Synthesis of α–Halo Amides via α, α–Dicyano Expoxides," *(Synthesis)* 229–232.

Wei Tang, 1995, "Fluorinated Analogues As Mechanistic Probes In Valproic Acid Hepatotoxicity: Comparative Metabolic And Pharmacokinetic Studies," *The University of British Columbia, Thesis* pp. ii–v, 31–45, 181–191, 236–241.

*Primary Examiner*—Deborah D. Carr
(74) *Attorney, Agent, or Firm*—Morgan & Finnegan

(57) ABSTRACT

Alpha-fluorinated alkynoic acids and pharmaceutical compositions containing these compounds are provided, which are useful for the treatment and prevention of seizures such as are associated with epilepsy. The compounds of the invention exhibit reduced side effects, relative to valproic acid, with regard to sedation and teratogenic potential.

23 Claims, 1 Drawing Sheet

ALPHA-FLUORO ALKYNOIC ACIDS WITH ANTICONVULSANT ACTIVITY

This is a continuation-in-part of now abandoned provisional application Ser. No. 60/090,270 filed Jun. 22, 1998.

FIELD OF THE INVENTION

This invention relates to fluorinated alkynoic acids, to the preparation thereof, and to the use thereof as anti-convulsive therapeutic agents. The fluorinated alkynoic acids of the invention are comparable to valproic acid in their utility for the prevention of seizures, but have reduced teratogenic potential. Consequently, this invention provides effective anti-epileptic agents with a greater margin of safety than valproic acid with respect to teratogenic potential. Certain compounds of this invention also exhibit comparable or reduced sedative effects relative to valproic acid, and certain compounds of the invention exhibit a longer duration of activity than valproic acid.

BACKGROUND OF THE INVENTION

Epilepsy affects roughly 1% of the world'population. Among the drugs employed for control of epileptic seizures is valproic acid. Valproic acid (also referred to as VPA, valproate, or 2-propylpentanoic acid) is an effective anticonvulsant, but it has a short duration of action. More seriously, VPA suffers from serious side effects, among them sedation, potentially fatal hepatotoxicity, and teratogenicity. Hepatotoxicity is particularly a problem in young children, especially children on polytherapy. The VPA-induced hepatic fatality rate among the latter patient category is reported to be 1/500 (F. E. Dreifuiss et al., Neurology (1987), 37, 379–385). Valproic acid has been shown to induce neural tube defects in mice, and it is estimated that the risk of spina bifida among newborns of women taking VPA during pregnancy is 1–2% (Centers for Disease Control, Morbidity and Mortality Weekly Report (1983), 32(33), 438–439).

There has been a considerable effort to discover analogues of valproic acid that are equally effective, but that have a greater margin of safety. See, for example, H. Nau et al., PCT application WO 94/06743, wherein a variety of modifications to the alkyl chains of valproic acid are made, and the related U.S. Pat. No. 5,786,380, which is hereby incorporated in its entirety by reference.

With regard to teratogenicity, it has been reported that introduction of a triple bond into the 4-position of valproic acid greatly increases teratogenicity, but that this effect is largely confined to the S-(−) enantiomer. Addition of a methyl group to the end of the triple bond abolished teratogenicity, while maintaining anticonvulsant activity (H. Nau, R.-S. Hauck, K. Ehlers, *Pharmacology & Toxicology* (1991), 69, 310–321.) These results indicated that separation of teratogenicity and anticonvulsive activity was possible. Sedative side effects were also separated from anticonvulsant activity in some analogues (M. Elmazar, R.-S. Hauck, H. Nau, *J. Pharm. Sci.* (1993), 82, 1255–1288.)

Alpha-branched carboxylic acids with an alpha-fluorine are little known. P. Crowley et al., in European patent application EP 468681, refers to 2-ethyl-2-fluorobutanoic acid as a fungicide intermediate, and a method for its preparation. Takeuchi refers to several examples of this class of compound in a publication relating to methods of preparing tertiary alkyl fluorides (Y. Takeuchi et al., *J. Org. Chem.* (1993), 58(13), 3483–3485).

The valproic acid analogue 2-fluoro-2-propyl-4-pentenoic acid has also been reported. The compound was used as a probe for studies of valproic acid hepatotoxicity and metabolism. (W. Tang et al., *Chem. Res. Toxicol.* (1995), 8(5), 671–682; M. Jurima-Romet et al., *Toxicology* (1996), 112(1), 69–85; W. Tang and F. Abbott, *Drug Metab. Dispos.* (1997), 25(2), 219–227.) In the above references, the presence of the 2-fluoro substituent was reported to reduce hepatotoxicity relative to 2-propyl-4-pentenoic acid. Anticonvulsant, sedative or teratogenic properties of the fluorinated compound were not disclosed.

Alpha-fluorinated valproic acid, 2-fluoro-2-propylpentanoic acid, has also been reported (Ph.D. thesis of Wei Tang, University of British Columbia, 1996). The anticonvulsant activity and pharmacokinetics of this compound were studied, and its pharmaceutical potential was speculated upon (F. Abbott, W. Tang, J. Palaty, *J. Pharmacol. Exp. Ther.* (1997), 282, 1163–1172). The compound was reported to be less potent than VPA, and the hepatotoxic, sedative, or teratogenic properties were not disclosed.

Valproic acid analogues with terminal trifluoromethyl groups have been reported: 5,5,5-trifluoro-2-(3,3,3-trifluoropropyl) pentanoic acid (K. Yamaguchi and M. Taninaka, Japanese patent Application 4–21652 (1992), and 5,5,5-trifluoro-2-n-propyl pentanoic acid (Hiroshima et al., *Japan. J. Psychopharmacol.* (1992) 12, 427). These compounds, too, are less potent than VPA.

SUMMARY OF THE INVENTION

This invention relates to 2-fluoro-2-alkyl-4-alkynoic acid compounds, pharmaceutical compositions containing them, and their use to treat or prevent convulsions. This invention also provides processes for the preparation of these compounds. The preferred 2-fluorinated carboxylic acids of the invention possess anticonvulsant activity comparable or superior to that of valproic acid, but exhibit reduced teratogenicity, and a longer duration of activity as well.

The compounds of this invention may also be used to treat and/or prevent affective disorders such as for example bipolar depression, especially the manic phase; and migraine, especially for prophylaxis of attacks.

The compounds of the invention have the following structure:

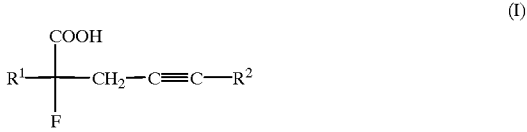

(I)

wherein $R^1$ is $C_3$ to $C_{10}$ alkyl, $C_3$ to $C_6$ cycloalkyl, or cyclopropylmethyl, and $R^2$ is $C_1$ to $C_3$ alkyl or cyclopropyl, and the pharmaceutically acceptable salts, esters, and amides thereof. The term alkyl as used herein refers to both branched and straight-chain alkyl groups. Preferred embodiments of this invention are those wherein $R^2$ is methyl. $R^1$ is preferably $C_3$ to $C_8$ alkyl, and more preferably $C_3$ to $C_5$ alkyl. In the most preferred embodiments, $R^2$ is methyl and $R^1$ is $C_3$ to $C_5$ alkyl.

The invention also provides a method of treating and/or preventing convulsions due to a variety of causes, by administering to an individual in need of such treatment a therapeutically or prophylactically effective amount of at least one of the compounds of the invention.

An object of this invention is to provide compounds useful for preventing or reducing seizure activity.

Another object of this invention is to provide anticonvulsant pharmaceutical compositions comprising at least one compound of this invention.

Yet another object of this invention is to provide methods of preventing or reducing seizure activity by administering to an individual in need of such treatment a pharmaceutical composition of this invention.

DETAILED DESCRIPTION OF THE INVENTION

Figure 1:
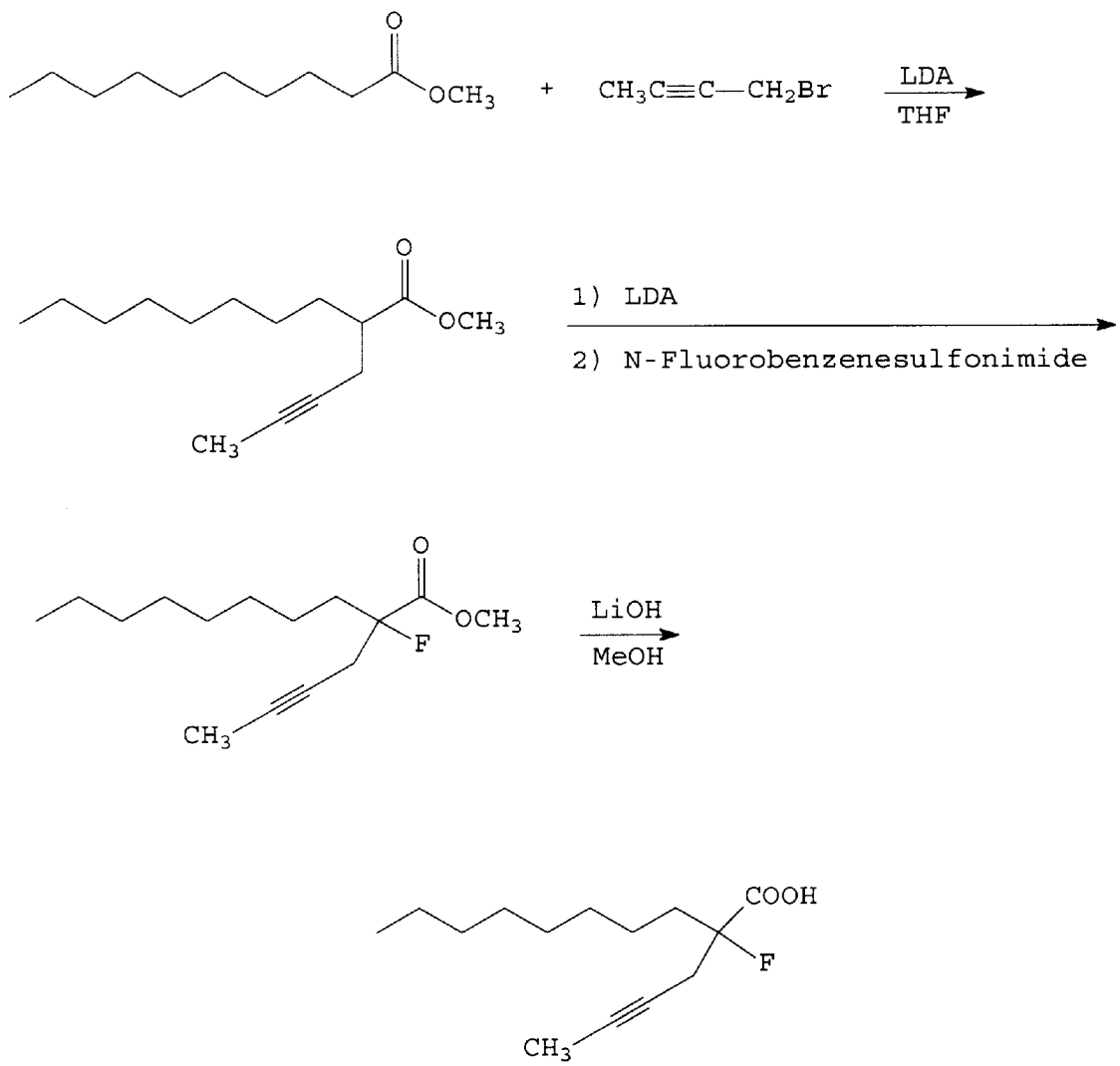
FIG. 1 is an example of a method for preparing the compounds of this invention.

This invention provides compounds having the following structure:

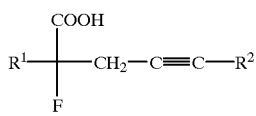
(I)

wherein $R^1$ is $C_3$ to $C_1$ alkyl, $C_3$ to $C_6$ cycloalkyl, or cyclopropylmethyl, and $R^2$ is $C_1$ to $C_3$ alkyl or cyclopropyl, and the pharmaceutically acceptable salts, esters, and amides thereof. The term alkyl as used herein refers to both branched and straight-chain alkyl groups. Preferred embodiments of this invention are those wherein $R^2$ is methyl. $R^1$ is preferably $C_3$ to $C_8$ alkyl, and more preferably $C_3$ to $C_5$ alkyl. In the most preferred embodiments, $R^2$ is methyl and $R^1$ is $C_3$ to $C_5$ alkyl.

These compounds can be prepared by methods known in the art for the preparation of other alpha-fluoro carboxylic acids. For example, treatment of the corresponding alpha-hydroxy ester with diethylaminosulftir trifluoride (DAST) provides the alpha-fluoro ester, which upon hydrolysis provides the acid (P. Crowley et al., 1992, European patent application EP 468681). Alternatively, the corresponding alpha-amino acid can be subjected to diazotization in the presence of fluoride ion, to effect a deaminative fluorination (J. Barber, R. Keck, J. Retey, *Tetrahedron Letters* (1982), 23, 1549–1552). The Reformatsky reaction can be carried out on alpha-bromo-alpha-fluoro esters (Y. Takeuchi et al., *J. Org. Chem.* (1993), 58(13), 3483–3485) to introduce a side chain. Alternatively, the corresponding ester enolate or silyl enol ether can be fluorinated with fluorine or a "positive fluorine" source, such as an N-fluoro pyridinium salt, N-fluoro amide, or N-fluoro imide (see, e.g., E. Differding, G. Ruegg, *Tetrahedron Letters* (1991), 32, 3815–3818). In the particular embodiment exemplified below, the lithium enolate of the corresponding ester is fluorinated with N-fluoro benzenesulfonimide, but it will be understood that other methods of synthesis are within the scope of this invention.

The starting esters for the exemplified process are in many cases commercially available; alternatively they may be obtained by methods known in the art, for example the malonic ester synthesis described in M. Elmazar, R.-S. Hauck, H. Nau, *J. Pharm. Sci.* (1993), 82, 1255–1288. The well-known acetoacetate variation of the malonic ester synthesis is also applicable. In the example below, direct alkylation of a straight-chain ester enolate is employed. Other methods of synthesis will be apparent to those skilled in the art, and this invention is not limited by the particular synthetic method exemplified herein.

In general terms, this invention provides a process for preparation of compounds of structure I, which comprises the steps of:

a) alkylating a compound of structure

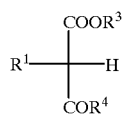
(II)

wherein $R^3$ is lower alkyl or benzyl and $R^4$ is H, lower alkyl, lower alkoxy, or benzyloxy, with an alkylating reagent of structure

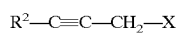
(III)

wherein X is a suitable leaving group, and wherein $R^2$ is $C_1$ to $C_3$ alkyl or cyclopropyl, in the presence of a suitable base, so as to obtain a compound of structure

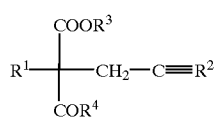
(IV)

(b) in the cases where $R^4$ is lower alkoxy or benzyloxy, hydrolysis, decarboxylation, and re-esterification of compound IV; or in cases where $R^4$ is H or lower alkyl, deacylation of compound IV, so as to obtain a compound of structure

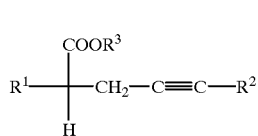
(V)

(c) enolization of compound V with a suitable base, in an inert solvent;
(d) addition of a fluorinating reagent, so as to obtain a compound of structure

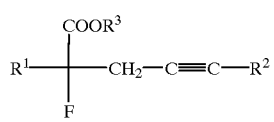
(VI)

and
(e) hydrolysis of the ester moiety.

Suitable identities of group $R^4$ will be apparent to those skilled in the art. Preferred $R^4$ groups are alkoxy groups which are readily saponified, such as methoxy or ethoxy, or other carboxylic acid protecting groups which are readily removed by other means, such as tert-butoxy, benzyloxy, and the like. It will be appreciated that the term "hydrolysis" as used in steps (b) and (e) is intended to encompass the deprotecting operations appropriate to the nature of $R^4$, for example saponification in the case of lower alkoxy groups, acidolysis in the case of tert-butoxy groups or hydrogenolysis in the case of benzyloxy groups. Similar considerations apply to the group $R^3$, which is preferably lower alkyl such as methyl or ethyl but which may be another carboxy-protecting group, such as for example, tert-butyl, benzyl, and the like. It will be apparent that in step (b), where $R^3$ is removed and then re-introduced, the practitioner will have the opportunity to change the identity of $R^3$ if it is desired to do so.

Where $R^4$ is H or alkyl, the preferred groups are those which lend themselves to deacylation of the group $COR^4$; in these cases $R^4$ is most preferably H or methyl. Deacylation may be accomplished by treatment with, for example, sodium hydroxide or ammonia, or other methods known in the art.

Suitable leaving groups X may be selected from, but are not limited to, the halogens chlorine, bromine, or iodine, or sulfonate ester groups such as methanesulfonyloxy or toluenesulfonyloxy. Suitable bases for step (a) may be chosen from, but are not limited to, alkali metal alkoxides, calcium and magnesium alkoxides, alkali metal hydrides, and the like.

Suitable bases for step (c) will be apparent to those skilled in the art, since a number of procedures for enolizing esters have been published. Preferred bases will be those with a sufficiently high $pK_a$ to substantially deprotonate the compound V, and which are also non-reactive with the functional groups of the compound V. Examples may be chosen from, but are not limited to, the lithium or sodium salts of hindered disubstituted amines, such as lithium diisopropylamide or lithium hexamethyldisilazide.

In an alternative process, compounds of formula (I) may be prepared by the process comprising the steps of:

a) alkylating a compound of structure

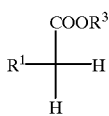

(VII)

wherein $R^3$ is lower alkyl or benzyl with an alkylating reagent of structure

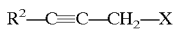

(III)

wherein X is a suitable leaving group, and wherein $R^2$ is $C_1$ to $C_3$ alkyl or cyclopropyl, in the presence of a suitable base, so as to obtain a compound of structure

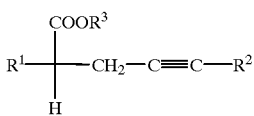

(V)

(b) enolization of compound V with a suitable base, in an inert solvent;

(c) addition of a fluorinating reagent, so as to obtain a compound of structure

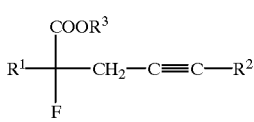

(VI)

and (d) hydrolysis of the ester moiety.

Modifications to the exemplified procedures can also be made. For example, in the fluorination step, inert solvents other than THF may be employed, such as dioxane, di-alkyl ethers, dimethoxyethane and other polyethers, toluene, heptane, and the like. Additives such as hexamethylphosphoramide, tetramethylethylenediamine, or tetramethylurea can be employed in the alkylation and fluorination reactions, and as described above a variety of bases such as alkali metal hydride, amide, alkoxide, or hexamethyldisilazide salts could be employed in the deprotonation and enolization reactions.

Alpha-fluorination of a straight-chain alkyl or alkynyl ester, acid, or amide prior to alkylation might also be carried out, if deemed desirable by the practitioner. Such modifications could be made for any reason, for example to improve the yield or to reduce process costs, without departing from the scope of this invention.

By the methods exemplified or described herein, the following compounds may be prepared from the appropriate starting materials, which may be chosen based upon the principles disclosed above:

Example 1  2-ethyl-2-fluoro-4-hexynoic acid
Example 2  2-cyclopropyl-2-fluoro-4-hexynoic acid
Example 3  2-fluoro-2-n-propyl-4-hexynoic acid
Example 4  2-n-butyl-2-fluoro-4-hexynoic acid
Example 5  2-fluoro-2-n-pentyl-4-hexynoic acid
Example 6  2-fluoro-2-n-hexyl-4-hexynoic acid
Example 7  2-fluoro-2-n-heptyl-4-hexynoic acid
Example 8  2-fluoro-2-n-octyl-4-hexynoic acid
Example 9  2-ethyl-2-fluoro-4-heptynoic acid
Example 10  2-fluoro-2-n-propyl-4-heptynoic acid
Example 11  2-n-butyl-2-fluoro-4-heptynoic acid
Example 12  2-fluoro-2-n-pentyl-4-heptynoic acid
Example 13  2-fluoro-2-n-hexyl-4-heptynoic acid
Example 14  2-fluoro-2-n-heptyl-4-heptynoic acid
Example 15  2-fluoro-2-n-octyl-4-heptynoic acid
Example 16  2-fluoro-2-n-propyl-4-cyclopropyl-4-pentynoic acid.
Example 17  2-cyclopropylmethyl-2-fluoro-4-hexynoic acid In one embodiment of this invention, these acids are provided in the form of pharmaceutically acceptable salts or prodrugs. Salt forms may be employed, for example, in order to obtain more crystalline materials, for purposes of ease of manufacturing or formulating, or they may be employed where more water-soluble forms of the compounds are desirable, for example in parenteral or oral liquid formulations. Both salt and pro-drug forms may be employed in order to improve the bioavailability or pharmacodynamics of a preparation.

Suitable salts are, for example, tris(hydroxymethyl)-ammonium, ammonium, sodium, potassium, calcium, and magnesium salts. Salt forms may be prepared by methods well-known in the art, for example by neutralization or by ion exchange. Compositions derived from partial neutralization of the acid are also contemplated to be within the scope of this invention. In general, suitable pharmaceutically acceptable salt forms, and methods for their preparation, will be apparent to those skilled in the art.

Suitable prodrugs are, for example, lower alkyl esters, alkoxy-alkyl esters, hydroxy-alkyl esters, and amides. The preferred lower alkyl esters are $C_1$ to $C_4$ alkyl esters. The amides may be unsubstituted on nitrogen, or may carry one or two nitrogen substituents such as alkyl, alkoxy-alkyl, hydroxy-alkyl, amino-alkyl, and the like.

Combinations of drug and pro-drug compounds, for example in compositions intended to provide both rapid onset and prolonged activity, will be apparent to those skilled in the art, and are contemplated to be within the scope of this invention.

It will be apparent to those skilled in the art that the compounds of the invention, and the salts and prodrugs thereof, may exist in enantiomeric forms. The pure enantiomers may be resolved from the racemate by methods well-known in the art, for example by fractional recrystallization of diastereomeric amine salts, by chromatography of diastereomeric derivatives, or by chiral column chromatography. Alternatively, enantiomeric forms may be prepared by chiral synthesis, for example by alkylation or fluorination of chiral hydrazones (R.-S. Hauck, H. Nau, 1989, *Toxicology Letters*, 49, 41–48) or by alkylation or fluorination of chiral oxazolidinone derivatives (H. Nau et al., 1994, PCT International Application WO 94/06743). The R and S enantiomers, the racemates, and non-racemic mixtures of enantiomers are all contemplated to be within the scope of this invention.

Another object of this invention is to provide a method of treating individuals with epilepsy, or others in need of anticonvulsant therapy, with compounds of formula I or salts and prodrugs thereof. Mammals, and in particular humans, who would benefit from this method of treatment include those exhibiting, or at risk for exhibiting, any type of seizure. For example, the methods of this invention are useful for treating individuals with idiopathic generalized seizures such as absence, myoclonic and tonic-clonic seizures and partial seizures. Individuals suffering from epilepsy, in particular, are expected to benefit from administration of the compounds of this invention. The method of the invention comprises administering to an individual a therapeutically effective amount of at least one compound of formula I or a salt or prodrug thereof, which is sufficient to reduce or prevent seizure activity.

The dose of the compound used in the treatment of such disease will vary in the usual way with the seriousness of the disorder, the weight and metabolic health of the sufferer, and the relative efficacy of the compound employed. The preferred initial dose for the general patient population will be determined by routine dose-ranging studies, as are conducted for example during clinical trials. Therapeutically effective doses for individual patients may be determined by titrating the amount of drug given to the individual to arrive at the desired therapeutic or prophylactic effect while minimizing untoward side effects, as is currently done with valproic acid. Dosages may be similar to those used with VPA, however they may be adjusted appropriately, based on the potencies and kinetic parameters disclosed herein or as determined by routine methods. For example, the compound 2-fluoro-2-n-propyl-4-hexynoic acid (example 3) would be expected to be useful at dosages which are about 1.5 times greater than those used for VPA. A preferred initial dose for this compound, accordingly, may be estimated to be between about 10 and 100 mg/kg/day, more preferably between 20 and 50 mg/kg/day. This initial dose may be varied so as to obtain the optimum therapeutic effect in the patient. Generally, a dose of between 1 and 150 mg/kg/day of the compounds of the invention would be expected to be administered to an individual, either singly or in divided doses.

This invention also provides pharmaceutical compositions useful for providing anticonvulsant activity, which comprise at least one compound of the invention. In addition to comprising at least one of the compounds described by formula I or a salt or prodrug thereof, the pharmaceutical composition may also comprise one or more additives such as preservatives, excipients, fillers, wetting agents, binders, disintegrants, buffers, and carriers. Suitable additives may be for example magnesium and calcium carbonates, carboxymethylcellulose, starches, sugars, gums, magnesium or calcium stearate, coloring or flavoring agents, and the like. There exists a wide variety of pharmaceutically acceptable additives for pharmaceutical dosage forms, and selection of appropriate additives is a routine matter for those skilled in art of pharmaceutical formulation.

The compositions may be in the form of tablets, capsules, powders, granules, lozenges, suppositories, reconstitutable powders, or liquid preparations such as oral or sterile parenteral solutions or suspensions.

In order to obtain consistency of administration it is preferred that a composition of the invention is in the form of a unit dose. Unit dose forms for oral administration may be tablets, capsules, and the like, and may contain conventional excipients such as binding agents, for example syrup, acacia, gelatin, sorbitol, tragacanth, or polyvinylpyrrolidone; and carriers or fillers, for example lactose, sugar, maize-starch, calcium phosphate, sorbitol or glycine. Additives may include disintegrants, for example starch, polyvinylpyrrolidone, sodium starch glycolate or microcrystalline cellulose; preservatives, and pharmaceutically acceptable wetting agents such as sodium lauryl sulfate.

In addition to unit dose forms, multi-dosage forms are also contemplated to be within the scope of the invention. Delayed-release compositions, for example those prepared by employing slow-release coatings, micro-encapsulation, and/or slowly-dissolving polymer carriers, will also be apparent to those skilled in the art, and are contemplated to be within the scope of the invention.

The solid oral compositions may be prepared by conventional methods of blending, filling, tabletting or the like. Repeated blending operations may be used to distribute the active agent throughout those compositions employing large quantities of fillers. Such operations are conventional in the art. The tablets may be coated according to methods well known in normal pharmaceutical practice, for example with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol syrup, methyl cellulose, gelatin, hydroxyethylcellulose, carboxymethylcellulose, aluminum stearate gel, and hydrogenated edible fats; emulsifying agents, for example lecithin, sorbitan monooleate, or acacia; non-aqueous vehicles (which may include edible oils), for example almond oil or fractionated coconut oil, oily esters such as esters of glycerin, propylene glycol, or ethyl alcohol; preservatives, for example methyl or propyl p-hydroxybenzoate or sorbic acid; and if desired conventional flavoring or coloring agents.

For parenteral administration, fluid unit dosage forms are prepared utilizing the compound and a sterile carrier, and, depending on the concentration used, can be either suspended or dissolved in the carrier. In preparing solutions the compound can be dissolved in water or saline for injection and filter sterilized before filling into a suitable vial or ampoule and sealing. Advantageously, additives such as local anaesthetics, preservatives and buffering agents can be dissolved in the vehicle. Suitable buffering agents are, for example, phosphate and citrate salts. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by conventional means, for example by exposure to radiation or ethylene oxide, before being suspended in the sterile carrier. Advantageously, a surfactant or wetting agent is included in the composition to facilitate uniform distribution of the compound.

EXAMPLES

A. Preparation of the Compounds

Example 8: 2-fluoro-2-octyl-4-hexynoic acid.

A solution of 0.055 mol of lithium diisopropylamide (LDA) in 100 ml tetrahydrofuran (THF) was cooled to −78° C. under an inert atmosphere, and 0.055 mol of methyl decanoate in THF was added dropwise with stirring. The mixture was allowed to warm over one hour to −20° C., then cooled again to −78° C. A solution of 1-bromo-2-butyne (0.050 mol) in THF (20 ml) was added dropwise, and the mixture allowed to warm to room temperature overnight. Aqueous 6N HCl (100 ml) was added, and the product extracted with ethyl ether, dried with anhydrous sodium sulfate, concentrated, and distilled in vacuo to provide methyl 2-(2-butynyl)decanoate as an oil.

This ester was again deprotonated with LDA in THF, as described above, and at −78° C. a solution of N-fluoro benzenesulfonimide (1.1 equivalents) in THF was added dropwise. The mixture was allowed to warm to room temperature, quenched with saturated ammonium chloride solution, and worked up as above. Chromatography on silica gel with 5% ethyl acetate in hexane provided methyl 2-(2-butynyl)-2-fluorodecanoate as an oil.

The methyl ester (0.016 mol) was saponified by dissolving it in 30 ml of methanol, adding 10 ml of water and 0.016 mol of lithium hydroxide, and stirring at room temperature for 24 hours. The methanol was removed in vacuo, and the residue was extracted once with ethyl ether. The aqueous solution was then acidified with hydrochloric acid and extracted again with ether. The ether extract was worked up as above, and chromatographed on silica gel with 25% ethyl acetate in hexane to provide the title compound as an oil in 26% overall yield. $^1$H NMR (CDCl$_3$): δ0.84 (3H, t, J=7 Hz), 1.24 (12H, M), 1.76 (3H, t, J=2 Hz), 1.88 (2H, m), 2.70 (2H, m) 9.40 (1H, br).

Examples 1–7 and 9–17 are prepared by the same method, from the appropriate starting materials.

B. Biological Activities of the Compounds

The anti-convulsive activity of the compounds of the invention was determined by the PTZ convulsion test (E. Swinyard et al., 1969, "Laboratory Evaluation of Antiepileptic Drugs, Review of Laboratory Methods," *Epilepsia* 10, 107–119; E. Swinyard, J. Woodhead, in *Antiepileptic Drugs*, 2nd ed., D. Woodbury, J. Penry, C. Pippenger, eds., Raven Press, New York, 1982, 111–126). Briefly, animals were dosed intraperitoneally with the sodium salt of the compound to be tested, and then challenged after 15 minutes with a subcutaneous injection of pentylenetetrazole (65 mg/kg). The percentage of animals that were protected from seizure (defined as at least one episode of continuous seizure activity lasting at least five seconds) is reported in Table 1 as "Anticonvulsant Activity %".

The sedative activity of the compounds was determined by the "Rotorod" test (Dunham, Miya, 1957, *J. Am. Pharm. Assoc.*, 46, 208–209). Animals were dosed with the sodium salt of the compound to be tested, and after 15 minutes they were placed on the ROTOROD apparatus (Rotorod, Ugobasile, Italy). The percentage of animals that fell from the rod is reported as "Sedative Activity %" in Table 1.

The teratogenic potential of the compounds was determined by injecting pregnant animals on day 8 of gestation with the sodium salt of the compound to be tested, and by examining the fetuses on day 18 of gestation (H. Nau, 1985, *Toxicol. Appl. Pharmacol.*, 80, 243–250; H. Nau, W. Loscher, 1986, *Fund. Appl. Toxicol.*, 6, 669). The percent of fetuses exhibiting exencephaly is reported as "Teratogenic Activity %" in Table 1.

TABLE 1

Anti-convulsive activity sedation, and teratogenic potential.
(Doses in mmol/kg; see text for definitions of % activity)

| COMPOUND (EXAMPLE NO.) | ANTICONVULSIVE ACTIVITY % (DOSE) | SEDATIVE ACTIVITY % (DOSE) | TERATOGENIC ACTIVITY % (DOSE) |
|---|---|---|---|
| (3) | 20(1.5) | 0(1.5) | 2(3.0) |
| (5) | 80(1.5) | 40(1.5) | 1(1.5) |
| (7) | 60(0.5) | 100(1.5) | 0(1.0) |
| (8) | 40(0.25) | 100(1.5) | 0(0.5) |
| VPA | 60(1.0) | 40(1.5) | 50(3.0) |

While the examples presented above describe a number of embodiments of this invention, it is apparent that the compounds, compositions, and methods of this invention can be altered to provide alternative embodiments which nonetheless utilize the methods of this invention. That such alternative embodiments may not have been expressly presented is not to be considered a disclaimer of those alternative embodiments. Therefore, it will be appreciated that the scope of this invention is not limited to the specific embodiments which have been presented above by way of example, and that such alternative embodiments will be within the literal scope of the claims or will be equivalent thereto. All references cited herein are hereby incorporated by reference in their entirety.

What is claimed is:

1. A compound of structure

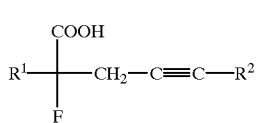

(I)

wherein R$^1$ is selected from the group consisting of C$_3$ to C$_{10}$ alkyl, C$_3$–C$_6$ cycloalkyl, and cyclopropylmethyl, and R$^2$ is selected from the group consisting of C$_1$ to C$_3$ alkyl and cyclopropyl; and pharmaceutically acceptable salts, esters, and amides thereof.

2. A compound selected from the group consisting of 2-ethyl-2-fluoro-4-hexynoic acid, 2-cyclopropyl-2-fluoro-4-hexynoic acid, 2-fluoro-2-n-propyl-4-hexynoic acid, 2-n-butyl-2-fluoro-4-hexynoic acid, 2-fluoro-2-n-pentyl-4-hexynoic acid, 2-fluoro-2-n-hexyl-4-hexynoic acid, 2-fluoro-2-n-heptyl-4-hexynoic acid, 2-fluoro-2-n-octyl-4-hexynoic acid, 2-ethyl-2-fluoro-4-heptynoic acid, 2-fluoro-2-n-propyl-4-heptynoic acid, 2-n-butyl-2-fluoro-4-heptynoic acid, 2-fluoro-2-n-pentyl-4-heptynoic acid, 2-fluoro-2-n-hexyl-4-heptynoic acid, 2-fluoro-2-n-heptyl-4-heptynoic acid, 2-fluoro-2-n-octyl-4-heptynoic acid, 2-fluoro-2-n-propyl-4-cyclopropyl-4-pentynoic acid, and 2-cyclopropylmethyl-2-fluoro-4-hexynoic acid; and pharmaceutically acceptable salts, esters, and amides thereof.

3. A compounds according to claim 1, wherein $R^2$ is methyl.

4. A compound according to claim 1, wherein $R^1$ is $C_6$ to $C_8$ alkyl.

5. A compound according to claim 1, wherein $R^2$ is methyl and $R^1$ is $C_6$ to $C_8$ alkyl.

6. A compound according to claim 1, wherein $R^2$ is methyl and $R^1$ is $C_3$ to $C_5$ alkyl.

7. The compound 2-fluoro-2-n-pentyl-4-hexynoic acid.

8. A method of reducing seizure activity in a mammal, comprising administering to said mammal a therapeutically effective amount of a compound according to claim 1.

9. The method of reducing seizure activity according to claim 8, wherein the compound is selected from the group consisting of 2-ethyl-2-fluoro-4-hexynoic acid, 2-cyclopropyl-2-fluoro-4-hexynoic acid, 2-fluoro-2-n-propyl-4-hexynoic acid, 2-n-butyl-2-fluoro-4-hexynoic acid, 2-fluoro-2-n-pentyl-4-hexynoic acid, 2-fluoro-2-n-hexyl-4-hexynoic acid, 2-fluoro-2-n-heptyl-4-hexynoic acid, 2-fluoro-2-n-octyl-4-hexynoic acid, 2-ethyl-2-fluoro-4-heptynoic acid, 2-fluoro-2-n-propyl-4-heptynoic acid, 2-n-butyl-2-fluoro-4-heptynoic acid, 2-fluoro-2-n-pentyl-4-heptynoic acid, 2-fluoro-2-n-hexyl-4-heptynoic acid, 2-fluoro-2-n-heptyl-4-heptynoic acid, 2-fluoro-2-n-octyl-4-heptynoic acid, 2-fluoro-2-n-propyl-4-cyclopropyl-4-pentynoic acid, and 2-cyclopropylmethyl-2-fluoro-4-hexynoic acid; and pharmaceutically acceptable salts, esters, and amides thereof.

10. The method of reducing seizure activity according to claim 8, wherein the compound is a compound according to claim 3.

11. The method of reducing seizure activity according to claim 8, wherein the compound is a compound according to claim 4.

12. The method of reducing seizure activity according to claim 8, wherein the compound is a compound according to claim 5.

13. The method of reducing seizure activity according to claim 8, wherein the compound is a compound according to claim 6.

14. The method of reducing seizure activity according to claim 8, wherein the compound is 2-fluoro-2-n-pentyl-4-hexynoic acid.

15. A pharmaceutical composition comprising at least one compound according to claim 1, in combination with at least one pharmaceutically acceptable additive.

16. A pharmaceutical composition comprising at least one compound according to claim 4, in combination with at least one pharmaceutically acceptable additive.

17. A pharmaceutical composition comprising at least one compound according to claim 6, in combination with at least one pharmaceutically acceptable additive.

18. A pharmaceutical composition comprising the compound 2-fluoro-2-n-pentyl-4-hexynoic acid, in combination with at least one pharmaceutically acceptable additive.

19. A process for preparing a compound of structure (I)

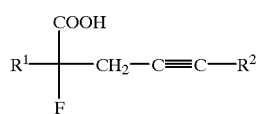

wherein $R^1$ is selected from the group consisting of $C_3$ to $C_{10}$ alkyl, $C_3$–$C_6$ cycloalkyl, and cyclopropylmethyl, and $R^2$ is selected from the group consisting of $C_1$ to $C_3$ alkyl and cyclopropyl, comprising the steps of:

(a) alkylating a compound of structure (II)

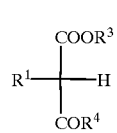

wherein $R^3$ is lower alkyl or benzyl and $R^4$ is H, lower alkyl, lower alkoxy, or benzyloxy, with an alkylating reagent of structure

   (III)

wherein X is a suitable leaving group, in the presence of a suitable base, so as to obtain a compound of structure (IV)

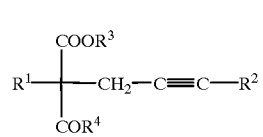

(b) where $R^4$ is lower alkoxy or benzyloxy, hydrolysis, decarboxylation, and re-esterification of compound IV, or where $R^4$ is H or lower alkyl, deacylation of compound IV, so as to obtain a compound of structure (V)

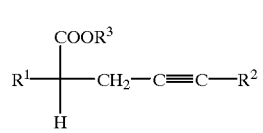

(c) enolization of compound V with a suitable base, in an inert solvent;

(d) addition of a fluorinating reagent, so as to obtain a compound of structure (VI)

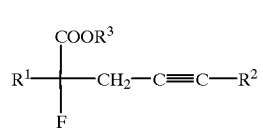

and (e) hydrolysis of the ester moiety.

20. The process of claim 19, wherein $R^4$ is lower alkoxy.

21. The process of claim 19, wherein the fluorinating reagent is an N-fluorosulfonimide.

22. A process for preparing a compound of structure

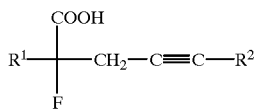 (I)

wherein $R^1$ is selected from the group consisting of $C_3$ to $C_{10}$ alkyl, $C_3$–$C_6$ cycloalkyl, and cyclopropylmethyl, and $R^2$ is selected from the group consisting of $C_1$ to $C_3$ alkyl and cyclopropyl, comprising the steps of:

a) alkylating a compound of structure

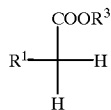 (VII)

wherein $R^3$ is lower alkyl or benzyl with an alkylating reagent of structure

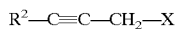 (III)

wherein X is a suitable leaving group, in the presence of a suitable base, so as to obtain a compound of structure

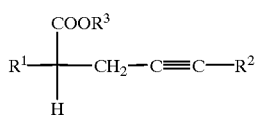 (V)

(b) enolization of compound V with a suitable base, in an inert solvent;

(c) addition of a fluorinating reagent, so as to obtain a compound of structure

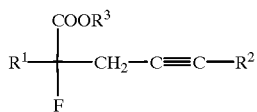 (VI)

and (d) hydrolysis of the ester moiety.

23. The process of claim 22, wherein the fluorinating reagent is an N-fluorosulfonimide.

* * * * *